(12) United States Patent
Ikuma et al.

(10) Patent No.: US 10,631,826 B2
(45) Date of Patent: Apr. 28, 2020

(54) MEDICAL APPARATUS, MEDICAL-IMAGE GENERATING METHOD, AND RECORDING MEDIUM ON WHICH MEDICAL-IMAGE GENERATING PROGRAM IS RECORDED

(71) Applicant: OLYMPUS CORPORATION, Tokyo (JP)

(72) Inventors: Soichi Ikuma, Akishima (JP); Zhen Li, Hino (JP); Makoto Ishikake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 378 days.

(21) Appl. No.: 15/682,788

(22) Filed: Aug. 22, 2017

(65) Prior Publication Data
US 2017/0347989 A1 Dec. 7, 2017

Related U.S. Application Data

(63) Continuation of application No. PCT/JP2016/067505, filed on Jun. 13, 2016.

(30) Foreign Application Priority Data

Jul. 6, 2015 (JP) .................................. 2015-135474

(51) Int. Cl.
*A61B 1/00* (2006.01)
*A61B 8/00* (2006.01)
(Continued)

(52) U.S. Cl.
CPC ................ *A61B 8/463* (2013.01); *A61B 1/00* (2013.01); *A61B 1/00009* (2013.01);
(Continued)

(58) Field of Classification Search
None
See application file for complete search history.

(56) References Cited

U.S. PATENT DOCUMENTS

2015/0173707 A1 6/2015 Ohuchi et al.
2015/0216392 A1 8/2015 Tojo et al.

FOREIGN PATENT DOCUMENTS

JP 2014-79377 A 5/2014
JP 2014-117446 A 6/2014
(Continued)

OTHER PUBLICATIONS

International Search Report dated Sep. 6, 2016 received in PCT/JP2016/067505.

*Primary Examiner* — Timothy J Neal
(74) *Attorney, Agent, or Firm* — Scully, Scott, Murphy & Presser, P.C.

(57) ABSTRACT

A medical apparatus includes a model-image generating section configured to generate a model image obtained by modeling a shape of an inside of a subject, a coordinate calculating section configured to detect a three-dimensional position of a feature point of the inside of the subject, set a polar coordinate on the basis of a position of the feature point, and calculate an arbitrary three-dimensional position of the inside of the subject according to the polar coordinate, and an image generating section configured to show the arbitrary three-dimensional position of the inside of the subject on the model image on the basis of one angle component among components of the polar coordinate calculated by the coordinate calculating section and a value obtained by correcting the one angle component according to another angle component.

9 Claims, 9 Drawing Sheets

(51) Int. Cl.
 *G02B 23/24* (2006.01)
 *A61B 1/307* (2006.01)
 *A61B 8/08* (2006.01)
 *G06T 7/00* (2017.01)
 *A61B 6/00* (2006.01)

(52) U.S. Cl.
 CPC ............ *A61B 1/307* (2013.01); *A61B 8/5207* (2013.01); *G02B 23/24* (2013.01); *G06T 7/0012* (2013.01); *A61B 6/466* (2013.01)

(56) References Cited

FOREIGN PATENT DOCUMENTS

| | | |
|---|---|---|
| JP | 2015-119768 A | 7/2015 |
| WO | 2014/061566 A1 | 4/2014 |

MEDICAL APPARATUS, MEDICAL-IMAGE GENERATING METHOD, AND RECORDING MEDIUM ON WHICH MEDICAL-IMAGE GENERATING PROGRAM IS RECORDED

CROSS REFERENCE TO RELATED APPLICATION

This application is a continuation application of PCT/JP2016/067505 filed on Jun. 13, 2016 and claims benefit of Japanese Application No. 2015-135474 filed in Japan on Jul. 6, 2015, the entire contents of which are incorporated herein by this reference.

BACKGROUND OF THE INVENTION

1. Field of the Invention

The present invention relates to a medical apparatus, a medical-image generating method, and a medical-image generating program for supporting endoscopic observation.

2. Description of the Related Art

In recent years, an endoscope apparatus functioning as a medical apparatus including an endoscope inserted into a subject to observe an inside of a subject and perform treatment using a treatment instrument and the like has been widely used. There is a medical apparatus that displays an observation range on an image when observing an inside of a predetermined luminal organ set as an observation (or examination) target using an endoscope.

In such a medical apparatus, measurement concerning an organ of a patient is performed to acquire measurement data of the organ beforehand to make it possible to display an observation position during observation on a model image estimated on the basis of the acquired measurement data.

For example, Japanese Patent Application Laid-Open Publication No. 2014-117446 proposes a technique for inserting an endoscope into an organ of a person, calculating a distance to the organ with a sensor provided at an endoscope distal end, and further providing a sensor for detecting a movement of the endoscope to estimate a shape of the organ from measurement results of the sensors and displacement of the endoscope and generate a model image on the site.

SUMMARY OF THE INVENTION

A medical apparatus according to an aspect of the present invention includes: a model-image generating section configured to generate a model image obtained by modeling a shape of an inside of a subject; a coordinate calculating section configured to detect a three-dimensional position of a feature point of the inside of the subject, set a polar coordinate on the basis of a position of the feature point, and calculate an arbitrary three-dimensional position of the inside of the subject according to the polar coordinate; and an image generating section configured to show the arbitrary three-dimensional position of the inside of the subject on the model image on the basis of one angle component among components of the polar coordinate calculated by the coordinate calculating section and a value obtained by correcting the one angle component according to another angle component.

A medical-image generating method according to an aspect of the present invention is a medical-image generating method in a medical apparatus including a position/direction acquiring section, a coordinate calculating section, a model-image generating section, and an image generating section, the medical-image generating method including: the position/direction acquiring section calculating an arbitrary three-dimensional position of an inside of a subject including a feature point of the inside of the subject; the coordinate calculating section setting a polar coordinate on the basis of a three-dimensional position of the feature point of the inside of the subject and calculating the arbitrary three-dimensional position of the inside of the subject according to the polar coordinate; the model-image generating section generating a model image obtained by modeling a shape of the inside of the subject; and the image generating section showing the arbitrary three-dimensional position of the inside of the subject on the model image on the basis of at least one angle component among components of the polar coordinate calculated by the coordinate calculating section and a value obtained by correcting the one angle component according to another angle component.

A recording medium on which a medical-image generating program is recorded according to an aspect of the present invention records the medical-image generating program for causing a computer to execute a procedure for: calculating an arbitrary three-dimensional position of an inside of a subject including a feature point of the inside of the subject; setting a polar coordinate on the basis of a three-dimensional position of the feature point of the inside of the subject and calculating the arbitrary three-dimensional position of the inside of the subject according to the polar coordinate; generating a model image obtained by modeling a shape of the inside of the subject; and showing the arbitrary three-dimensional position of the inside of the subject on the model image on the basis of one angle component among components of the polar coordinate calculated concerning the arbitrary three-dimensional position of the inside of the subject and a value obtained by correcting the one angle component according to another angle component.

DETAILED DESCRIPTION OF THE PREFERRED EMBODIMENT(S)

Embodiments of the present invention are explained in detail below with reference to the drawings.

First Embodiment

Figure 1:
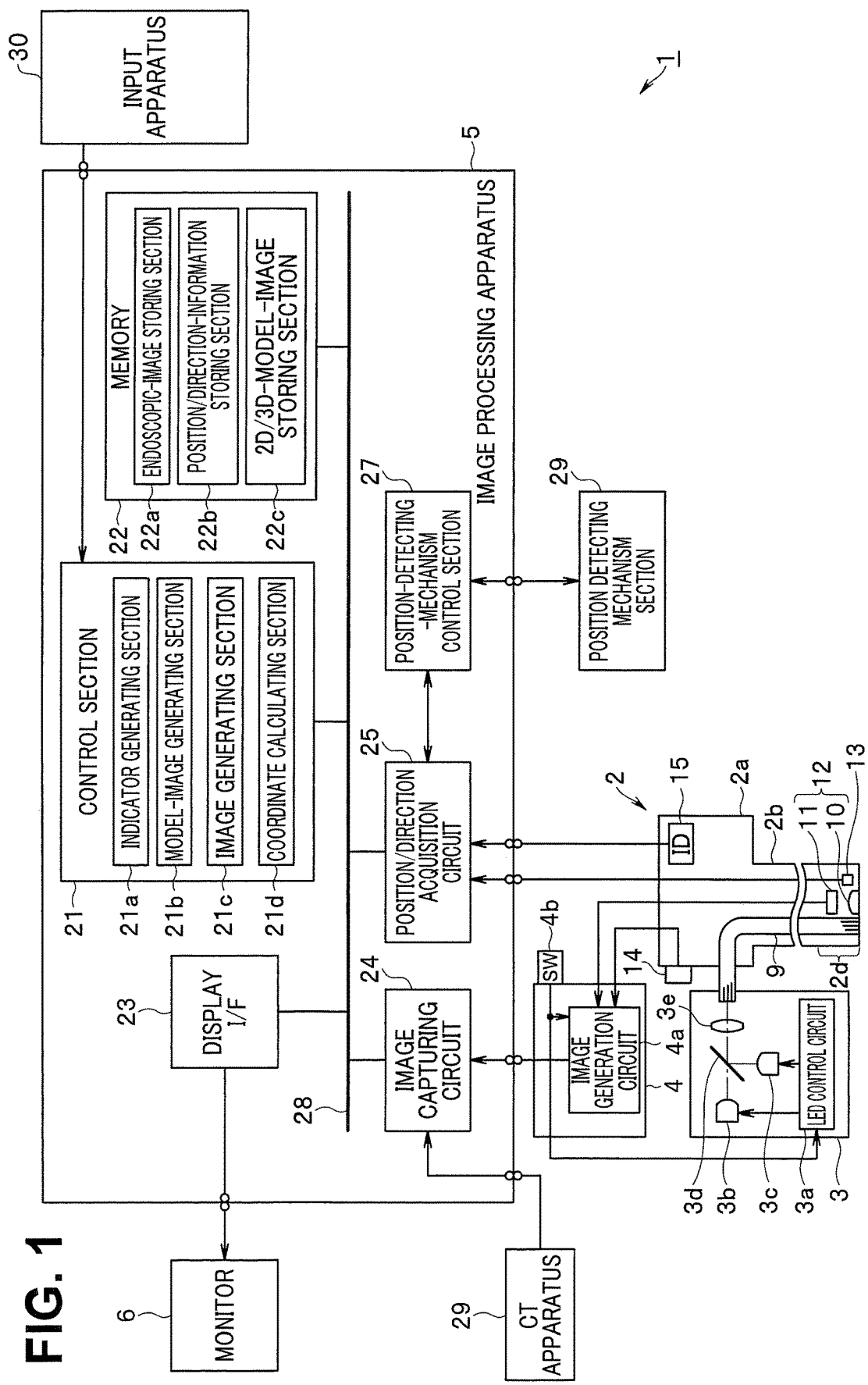
FIG. 1 is a block diagram showing a medical apparatus according to a first embodiment of the present invention.
Figure 2:
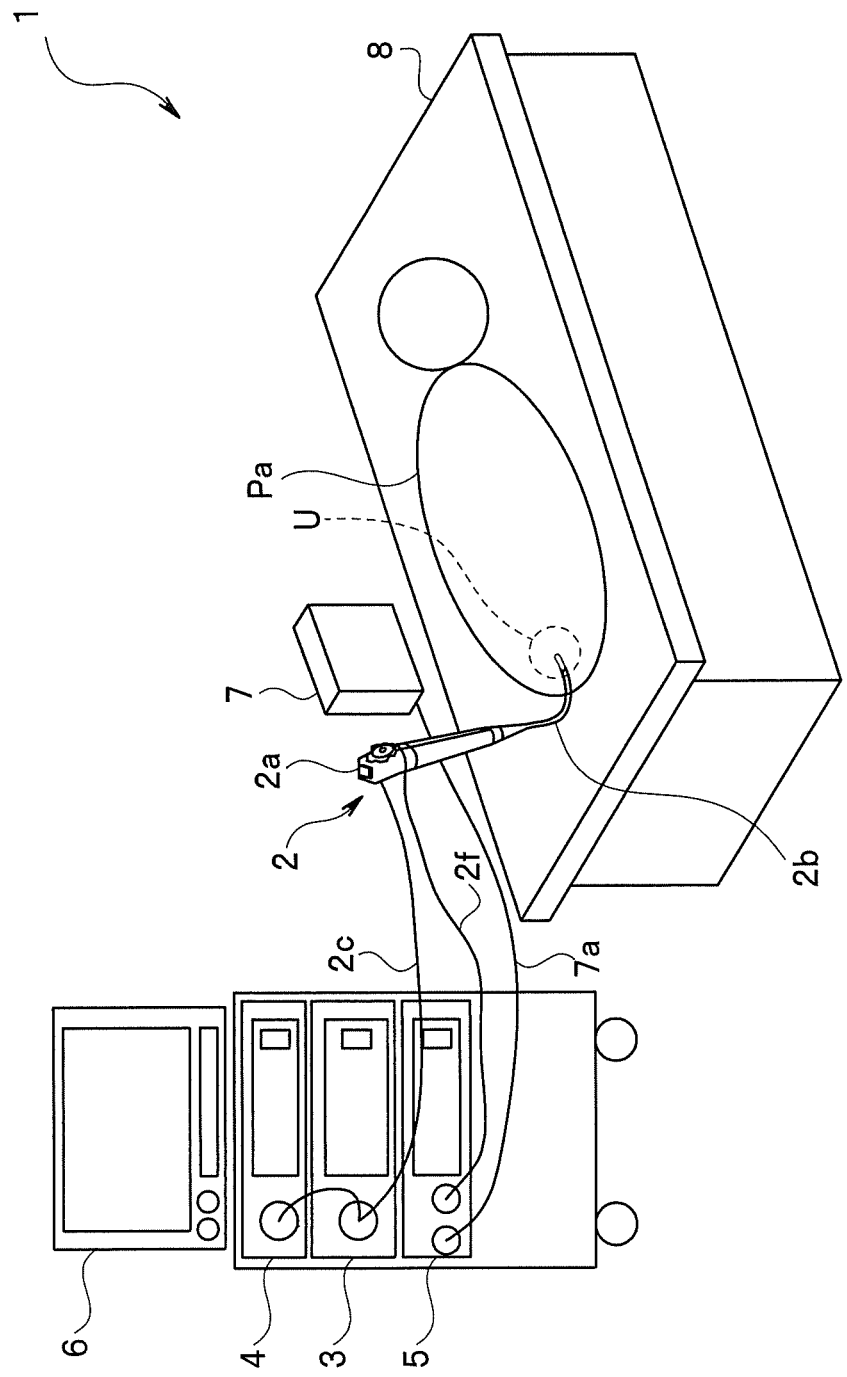
FIG. 2 is an explanatory diagram showing an exterior of the medical apparatus shown in FIG. 1.

FIG. 1 is a block diagram showing a medical apparatus according to a first embodiment of the present invention. FIG. 2 is an explanatory diagram showing an exterior of the medical apparatus shown in FIG. 1.

In general, a schema drawn on a paper medium schematically represents an actual shape of an organ. A schema having a common shape is often used in a paper clinical record or the like. A surgeon performs processing for writing, while taking into account a scale, an angle, and the like in a head, on a schema drawn on a paper surface, a position and a shape of a lesion part or the like obtained by actually performing observation with an endoscope or the like. Since the schema having the common shape different from an actual organ shape is used, it is sometimes easy for the surgeon to perform a check and the like of the lesion part.

Therefore, in the present embodiment, a common model image is used even when an observation range and the like are displayed in a model image displayed on a monitor. In this case, the present embodiment makes it possible to show an observation range and the like in an accurate position and an accurate range on the common model image irrespective of an individual difference of an organ shape and irrespective of deformation of an organ.

As shown in FIG. 2, a medical apparatus 1 performs observation of an inside of a subject. In the present embodiment, an example is explained in which an inside of a predetermined luminal organ (in a specific example, bladder U) an inside of a patient Pa is observed (or examined) as the inside of the subject. The medical apparatus 1 is configured to include an endoscope 2, which is an observation apparatus, a light source apparatus 3, a processor 4, an image processing apparatus 5, a monitor 6, and a position detecting mechanism section 29. The medical apparatus 1 may have a function of observing the inside of the subject in two observation modes, that is, a normal light observation and a special light observation. A surgeon acting as a user of the medical apparatus 1 performs an endoscopic examination of an inside of a bladder U serving as a predetermined luminal organ (simply referred to as luminal organ or organ as well) in a patient Pa lying on a bed 8 in a dorsal position or the like.

The endoscope 2 includes an operation section 2a, an insertion section 2b having flexibility, and a universal cable 2c. The endoscope 2 is, for example, an endoscope for a bladder examination. A light guide 9 shown in FIG. 1 is inserted through the universal cable 2c. The endoscope 2 emits illumination light of the light source apparatus 3 from an illumination window at a distal end portion 2d of the insertion section 2b through the light guide 9. The inside of the predetermined (bladder U serving as) luminal organ, which is the inside of the subject into which the distal end portion 2d of the insertion section 2b is inserted, is illuminated by the illumination light.

As shown in FIG. 1, an objective optical system 10 and an image pickup device 11 are provided at the distal end portion 2d of the insertion section 2b. An image pickup surface of the image pickup device 11 is disposed in an image forming position of the objective optical system 10. The image pickup device 11 photoelectrically converts a subject optical image formed on the image pickup surface and outputs the subject optical image as an image pickup signal. In this way, the image pickup device 11 picks up an image of an inner wall of the bladder U illuminated by the illumination light of the light source apparatus 3. An image pickup section (or an image pickup apparatus) 12 configured to pick up an image of the inside of the luminal organ and output a picked-up image is configured by the objective optical system 10 and the image pickup device 11.

The image pickup signal obtained by the image pickup device 11 is inputted to the processor 4 via a signal line in the universal cable 2c. An image generation circuit 4a is provided in the processor 4. The image generation circuit 4a performs image generation processing using the inputted image pickup signal and generates an endoscopic image (a picked-up image) of the inside of the bladder U serving as the luminal organ.

The image generation circuit 4a outputs the generated picked-up image to the image processing apparatus 5. An image capturing circuit 24 of the image processing apparatus 5 has a function of an image capturing section configured to perform processing for capturing, at a constant cycle, an endoscopic image generated in the processor 4. The image capturing circuit 24 acquires, for example, thirty endoscopic images in one second, which is the same as a frame rate, from the processor 4. The image capturing circuit 24 receives a release signal from the processor 4 as well. The image capturing circuit 24 captures a picked-up image from the image generation circuit 4a and gives the picked-up image to the monitor 6 via a display I/F 23. Consequently, an endoscopic image acquired by the endoscope 2 is displayed in an endoscopic image display area in the monitor 6. Note that the image capturing circuit 24 can capture an image from a CT apparatus 29 as well and supply the image to the monitor 6 via the display I/F 23.

The processor 4 includes a change over switch 4b for switching an observation mode. An observation mode signal designated by the change over switch 4b is inputted to the image generation circuit 4a. The image generation circuit 4a generates an endoscopic image corresponding to the observation mode designated by the change over switch 4b. More specifically, when the normal light observation mode is designated, the image generation circuit 4a generates a normal light observation image picked up under illumination of (white light serving as) normal light. When the special light observation mode is designated, the image generation circuit 4a generates a special light observation image (in a narrower sense, a narrow-band light observation image).

The observation mode signal designated by the change over switch 4b is inputted to an LED control circuit 3a of the light source apparatus 3 as well. The LED control circuit 3a controls LEDs 3b and 3c to generate illumination light corresponding to the observation mode. That is, when the normal light observation mode is designated by the change over switch 4b, the LED control circuit 3a controls a white LED 3b, which is a light source for the normal light observation mode, to emit light. When the special light observation mode is designated, the LED control circuit 3a controls a narrow-band blue LED 3c, which is a light source for the special light observation mode, to emit light.

When the narrow-band blue LED 3c emits light, narrow-band blue light is selectively reflected by a dichroic mirror 3d disposed at an angle of 45 degrees on an optical path of the blue light and thereafter condensed by a condensing lens 3e and made incident on a proximal end of the light guide 9. Narrow-band blue illumination light made incident on the proximal end of the light guide 9 is transmitted by the light guide 9 and emitted from an illumination window to which a distal end of the light guide 9 is attached. In this way, in this case, illumination for the special light observation mode (in a narrower sense, illumination for a narrow-band light observation mode) is performed.

When the white LED 3b emits light, most of white light excluding the narrow-band blue light is selectively transmitted by the dichroic mirror 3d disposed on an optical path of the white light, condensed by the condensing lens 3e, and made incident on the proximal end of the light guide 9. White illumination light excluding the narrow-band blue light made incident on the proximal end of the light guide 9 is transmitted by the light guide 9 and emitted from the illumination window attached to the distal end of the light guide 9. In this way, in this case, illumination in the normal light observation mode is performed.

In the operation section 2a of the endoscope 2, a release button (or a release switch) 14 is provided. The release button 14 is a button that the user such as the surgeon presses when recording (or storing) an endoscopic image. When the release button 14 is pressed, a release button operation signal is inputted to the processor 4. The processor 4 generates a release signal and outputs the release signal to the image processing apparatus 5. When the release button 14 is pressed, an endoscopic image is recorded (or stored) in a memory 22 explained below of the image processing apparatus 5. The medical apparatus 1 also includes an input apparatus 30 on which the user performs an input of various kinds of information and an input for selection to the image processing apparatus 5.

The image processing apparatus 5 has a function of causing the monitor 6 to display an endoscopic image, displaying a model image corresponding to an observation target, and displaying a photographing range and the like of the endoscopic image on the model image. The image processing apparatus 5 displays an endoscopic image generated by the processor 4 in a part of a display region on a display screen of the monitor 6 and displays the model image in another part of the display region. The image processing apparatus 5 displays an indicator indicating a range of an image of the displayed endoscopic image (a photographing range) on the model image displayed on the display screen.

The image processing apparatus 5 includes a control section 21, the memory 22, the display interface (hereinafter abbreviated as display I/F) 23, an image capturing circuit 24, a position/direction acquisition circuit 25, and a position-detecting-mechanism control section 27. The CPU 21, the memory 22, the display I/F 23, the image capturing circuit 24, and the position/direction acquisition circuit 25 are connected to one another via a bus 28. An endoscopic image is supplied from the image capturing circuit 24 to the control section 21 via the bus 28.

The memory 22 functioning as a storing section is configured by a ROM, a RAM (random access memory), a flash memory, or the like. The memory 22 stores various processing programs executed by the control section 21 and various data. The memory 22 includes an endoscopic-image storing section 22a configured to store information concerning an endoscopic image generated by the image generation circuit 4a and a position/direction-information storing section 22b configured to store position information and line-of-sight direction information acquired by the position/direction acquisition circuit 25. The memory 22 includes a 2D/3D-model-image storing section 22c configured to store image data of two-dimensional (2D) and three-dimensional (3D) model images. In the present embodiment, as the model images, a model image having a common shape is used irrespective of a patient and irrespective of a state of an organ.

The control section 21 can be configured by a not-shown processor such as a CPU. The control section 21 may operate according to a program stored in the memory and control the respective sections. A photographing range of an endoscopic image is calculated and display of a model image and display of an indicator indicating a photographing range on the model image are controlled by the control section 21.

In the present embodiment, a photographing range of the endoscope 2, which is an observation apparatus, that is, a range of an image displayed in a display region of an endoscopic image of the monitor 6 is calculated and accurately displayed in a common model image. Therefore, first, the position/direction acquisition circuit 25 detects a position and a direction of the image pickup device 11. The position detecting mechanism section 29 is configured to detect the position and the direction of the image pickup device 11. The position-detecting-mechanism control section 27 can control the position detecting mechanism section 29 to detect the position and the direction of the image pickup device 11 and can output a detection result to the position/direction acquisition circuit 25.

A publicly-known method can be adopted as the position detecting mechanism section and the position-detecting-mechanism control section. For example, a method may be adopted in which a not-shown receiving coil is provided at a distal end of the insertion section 2b as the position detecting mechanism section, a magnetic field transmission antenna configured to generate a magnetic field is provided on an outside of the endoscope 2, a signal of the receiving coil that receives the magnetic field from the magnetic field transmission antenna is analyzed, a position and a direction of the receiving coil are detected, and a position and a direction of the image pickup device 11 are detected from a known positional relation between the receiving coil and the image pickup device 11. A method described in Japanese Patent Application Laid-Open Publication No. 2014-117446 may be used. Data outputted by the position/direction acquisition circuit 25 is outputted in a coordinate system based on the magnetic field transmission antenna in the former case.

Subsequently, the position/direction acquisition circuit 25 calculates a distance from the image pickup device 11 to an observation target. The insertion section 2b of the endoscope 2 can bend, with a not-shown mechanism, a bending section present at the distal end of the insertion section 2b according to operation of an operation lever of the operation section 2a. For example, at the distal end of the insertion section 2b of the endoscope 2, a distance sensor 13 configured to measure a distance between the insertion section 2b and a surface of the bladder U of the patient Pa (an endoscope-inserted body inner surface) and output distance information is provided.

The distance sensor 13 is provided to measure a distance in a direction substantially parallel to a direction of an image pickup center of image pickup by the image pickup device 11. The position and the direction of the image pickup device 11 may be considered substantially the same as a position and a direction of the distance sensor 13. Consequently, it is possible to detect a distance to the endoscope-inserted body inner surface in a direction same as a direction of image pickup by the image pickup device 11.

For example, the distance sensor 13 may emit infrared laser light, detect the infrared laser light reflected on the endoscope-inserted body inner surface, and measure a position of the distance sensor 13, that is, a distance from the distal end of the insertion section 2b to the endoscope-inserted body inner surface on the basis of a difference between an emission time period and a detection time period of the infrared laser light. Note that, instead of providing the distance sensor 13, the control section 21 can be configured to perform an image analysis of an endoscopic stereo image and calculate a distance.

A position and a direction of the insertion section 2b in which the distance sensor 13 is set can be moved by inserting and rotating operation of the insertion section 2b or bending operation by an operation lever 41 of the operation section 2a. Therefore, it is also possible to move a measurement point measured by the distance sensor 13. That is, it is possible to measure a distance between any insertion section distal end and distance measurement point in an operable range of the endoscope 2.

The distance sensor 13 outputs the distance information, which is a measurement result, to the position/direction acquisition circuit 25. The position/direction acquisition circuit 25 calculates an observation range of the endoscope 2 on the basis of the position and the direction of the image pickup device 11, the distance information from the distance sensor 13, and a view angle explained below.

In the present embodiment, the observation range of the endoscope 2 is calculated in a polar coordinate system in order to show the observation range on the common model image irrespective of an individual difference of a shape of the bladder U, which is an examination target organ, a change in a size involved in expansion or reduction, and the like.

(Polar Coordinate System)

The present embodiment makes use of a characteristic that, for example, in a bladder, a large intestine, and the like, even if there are individual differences in sizes and shapes, when deformation such as expansion or reduction occurs, the bladder, the large intestine, and the like are deformed in a substantially similar shape with a certain point set as a start point. In the present embodiment, a point serving as such a start point of deformation in an organ (hereinafter referred to as organ deformation center) is calculated and an observation range (coordinate) is represented by a polar coordinate having the calculated organ deformation center as an origin. In the following explanation, for simplification, an arbitrary point in the observation range is explained as an observation point.

For example, it is assumed that, when a predetermined observation point in the organ is observed from the origin of the polar coordinate, the organ expands or reduces. In this case, since the expansion or the reduction is performed in a similar shape centering on the origin of the polar coordinate, which is the organ deformation center, a distance from the origin to the observation point changes but a viewing direction does not change. That is, in order to specify which position in the organ is the observation point, distance information from the origin is unnecessary and only angle information of the polar coordinate has to be known. A position of a model image having a shape close to a spherical shape or a cylindrical shape of the bladder, the large intestine, and the like can be designated only by the angle information. Therefore, by calculating points of the organs according to the polar coordinate, it is possible to calculate positions of the model image corresponding to the points of the organs without using the distance information from the origin.

Taking the above into account, in the present embodiment, by representing the observation range in the polar coordinate system having the organ deformation center as the origin, the observation range and the like are accurately displayed on the common model image irrespective of an actual shape of the organ.

Figure 3:
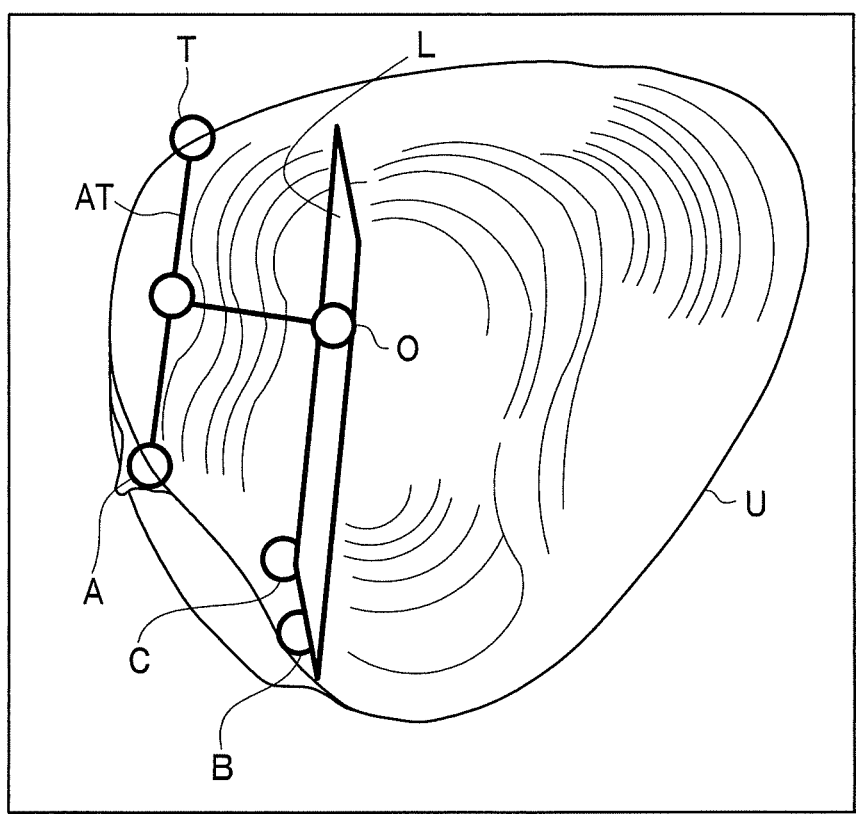
FIG. 3 is an explanatory diagram for explaining a method of calculating an organ deformation center.

A method of calculating the organ deformation center set as the origin of the polar coordinate is explained with reference to FIG. 3. FIG. 3 is an explanatory diagram for explaining the method of calculating the organ deformation center. In FIG. 3, an external shape of a bladder is indicated by a perspective view. Respective positions indicated by circles are respectively an internal urethral opening A, a left ureteral orifice B, a right ureteral orifice C, and a top T. In FIG. 3, the bladder U of the patient Pa in a lithotomy position is viewed from a left side slightly on a foot side and an abdomen side of the patient. In the present embodiment, the origin of the polar coordinate, which is the organ deformation center, is calculated from the internal urethral opening A, the left ureteral orifice B, the right ureteral orifice C, and the top T, which are four feature points of the bladder U. That is, a straight line AT connecting the top T of an abdomen and the internal urethral opening A is calculated and a plane L parallel to the straight line AT and passing the left and right ureteral orifices B and C is calculated. An origin O of the polar coordinate is set as a point obtained by projecting a midpoint of the straight line AT on the plane L.

Figure 4:
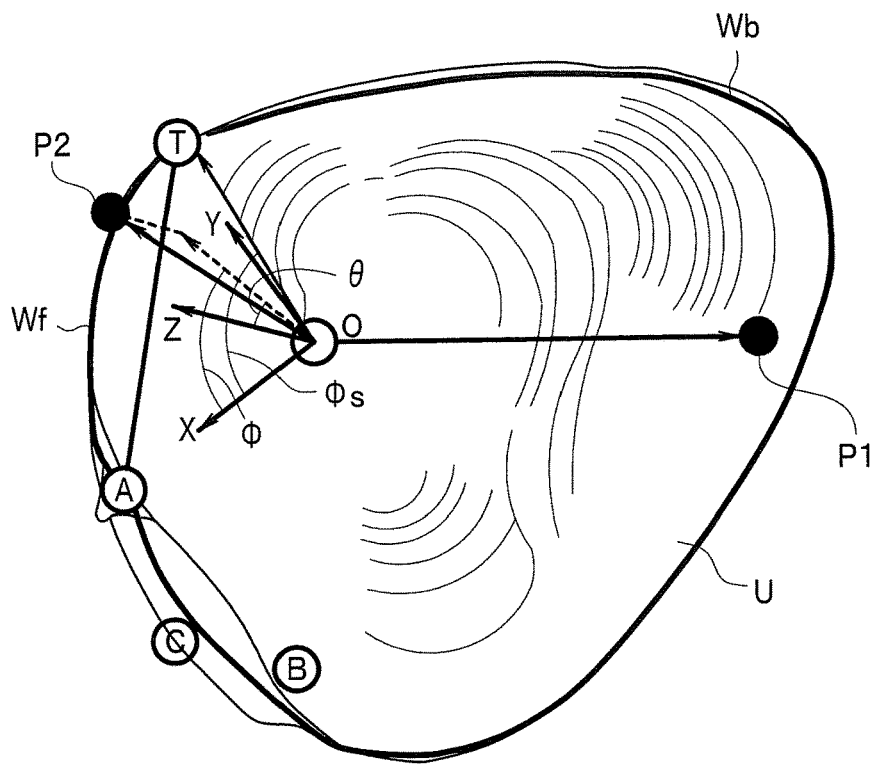
FIG. 4 is an explanatory diagram showing observation points in a polar coordinate.
Figure 5:
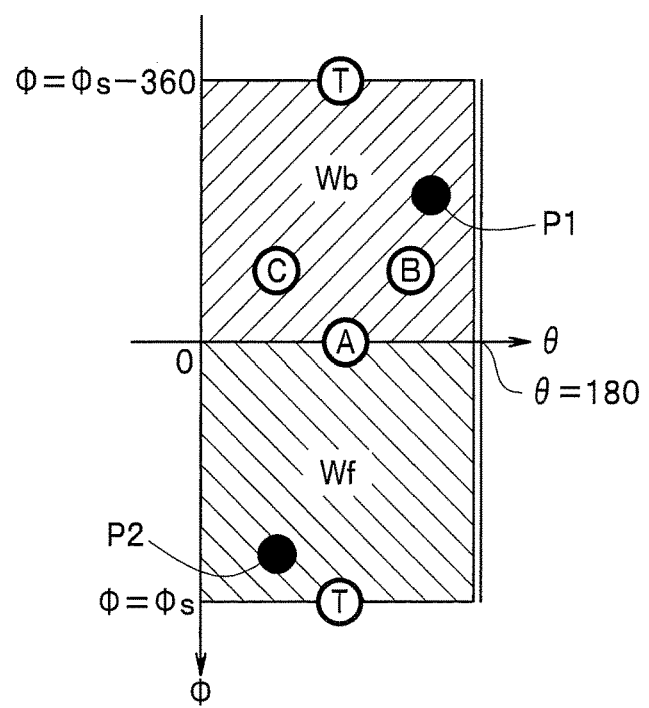
FIG. 5 is an explanatory diagram showing a two-dimensional model image with θ of the polar coordinate plotted on a horizontal axis and φ of the polar coordinate plotted on a vertical axis.
Figure 6:
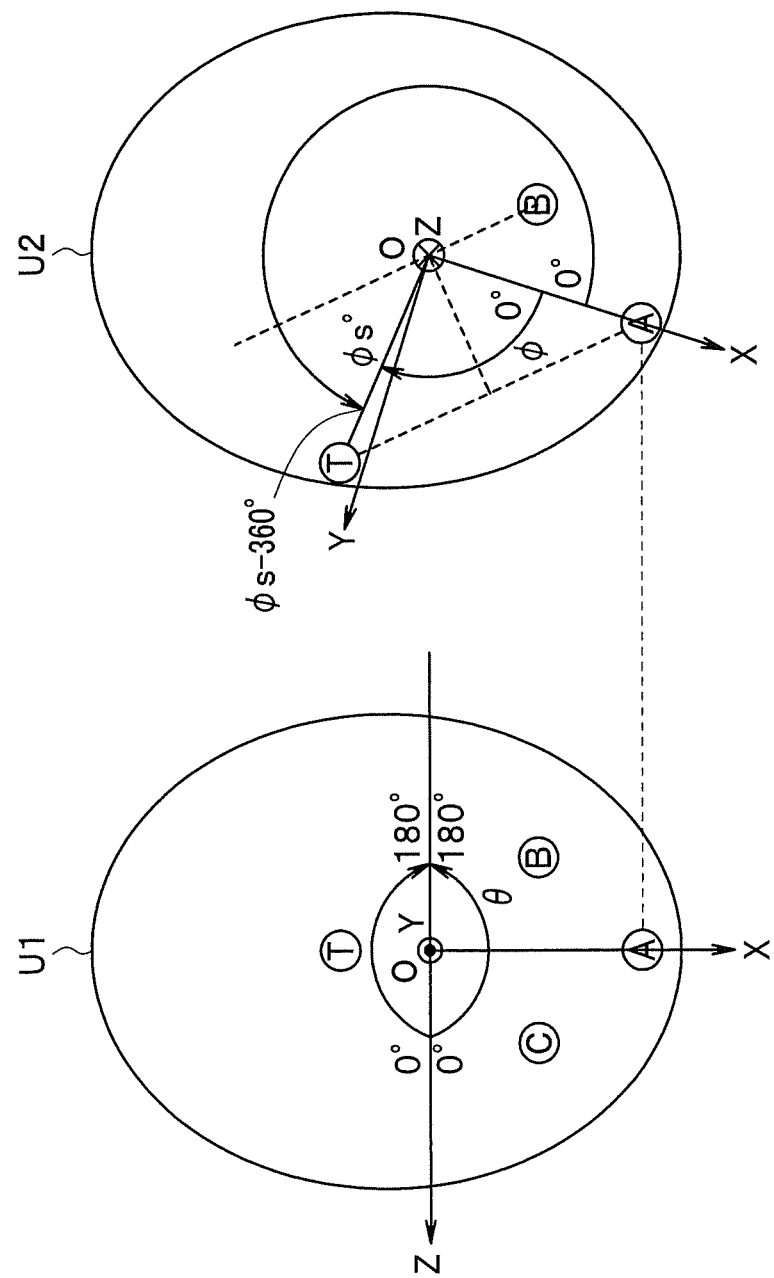
FIG. 6 is an explanatory diagram for schematically showing a plane shape U1 of a bladder in a state of a dorsal position and a side shape U2 of the bladder in a state of a right recumbent position and explaining correspondence between the polar coordinate and a model image.

A polar coordinate of a predetermined observation point on an organ wall surface and a relation between the polar coordinate and display on a model image are explained with reference to FIG. 4 and FIG. 5. FIG. 4 is an explanatory diagram showing observation points in the polar coordinate. FIG. 5 is an explanatory diagram showing a two-dimensional model image with θ of the polar coordinate plotted on a horizontal axis and φ of the polar coordinate plotted on a vertical axis. In the two-dimensional model image shown in FIG. 5, the bladder is divided into two of an anterior wall (Wf) and a posterior wall (Wb), which are respectively indicated by squares. FIG. 6 is an explanatory diagram for schematically showing a plane shape U1 of the bladder in a state in which a − direction is viewed from a + direction of a Y axis explained below and a side shape U2 of the bladder in a state in which a + direction is viewed from a − direction of a Z axis explained below and explaining correspondence between the polar coordinate and a model image. Note that, in the plane shape U1 shown in FIG. 6, the Y axis passes the origin and is a paper surface front direction. In the side shape U2, the Z axis passes the origin and is a paper surface depth direction.

In the present embodiment, X, Y, and Z axes of the polar coordinate are determined to correspond to coordinates of the two-dimensional model image. That is, as shown in FIG. 4 and FIG. 6, the Z axis of the polar coordinate is set in a direction extending from the left ureteral orifice B to the right ureteral orifice C passing the orgin O (a paper surface depth direction in FIG. 4). The X axis is set in a direction extending, from the orgin O, toward a point obtained by projecting the internal urethral opening A on a plane perpendicular to the Z axis and passing the orgin O. The Y axis is given by an outer product of Z and X. In the present embodiment, an example is shown in which a spherical coordinate among polar coordinates is used. In the spherical coordinate, a predetermined point is represented by (r, θ, φ), where r is a distance from the origin, $\theta$ is an angle from the Z axis, and $\phi$ is an angle from the X axis to a point obtained by projecting the predetermined point on an XY plane. Note that, in FIG. 6, an example is shown in which the internal urethral opening A is at $\theta$=90°. In this case, the X axis is in a direction extending from the orgin O to the internal urethral opening A on the plane perpendicular to the Z axis and passing the orgin O.

In the model image of the bladder shown in FIG. 5, a range on an abdomen side from the top T to the internal urethral opening A is represented by a square on a paper surface lower side as the anterior wall Wf. A remaining range on a back side is represented by a square on a paper surface upper side as the posterior wall Wb. A horizontal axis of the model image is equivalent to the angle $\theta$ from the Z axis shown in the plane shape U1 in FIG. 6. A vertical axis of the model image is equivalent to the angle $\phi$ from the X axis shown in the side shape U2 in FIG. 6.

For example, as shown in the plane shape U1 in FIG. 6, the angle $\theta$ from the Z axis of the internal urethral opening A is 90 degrees and the internal urethral opening A is present on the X axis. Therefore, as shown in the side shape U2, the angle $\phi$ from the X axis of the internal urethral opening A is 0°. The internal urethral opening A is shown in a boundary position between the anterior wall Wf and the posterior wall Wb on the model image shown in FIG. 5. Similarly, as shown in the side shape U2, an angle from the X axis of the top T is $\phi$s. The top T is shown in a position at a paper surface lower end of the model image shown in FIG. 5. An angle from the X axis of the top T is also $\phi$s−360. Therefore, the top T is shown in a position at a paper surface upper end of the model image shown in FIG. 5.

In this way, an observation point in the bladder U can be calculated as a coordinate position of the polar coordinate and a position on the model image can be indicated only by $\theta$ and $\phi$, which are angle information of the coordinate position. For example, it is assumed that polar coordinates of observation points P1 and P2 of a wall surface of the bladder U shown in FIG. 4 are respectively (r1, $\theta$1, $\phi$1) and (r2, $\theta$2, $\phi$2). In this case, the observation point P1 is displayed at a point of $\theta$=$\theta$1 and $\phi$=$\phi$1 of the model image shown in FIG. 5 and the observation point P2 is displayed at a point of $\theta$=$\theta$2 and $\phi$=$\phi$2 of the model image shown in FIG. 5.

Note that, as shown in FIG. 4, a breadth of the posterior wall Wb is relatively large compared with a breadth of the anterior wall Wf. However, in general, the breadths of the anterior wall Wf and the posterior wall Wb are set the same on a schema of a paper medium. Therefore, in the model image shown in FIG. 5, the breadths of the anterior wall Wf and the posterior wall Wb are set the same. Therefore, in the model image shown in FIG. 5, an angle per unit length is larger on a minus side (a paper surface upper side) than a plus side (a paper surface lower side) of the vertical axis. Note that a model image in which a size on the plus side and a size on the minus side are varied according to sizes of the anterior wall Wf and the posterior wall Wb may be adopted.

Incidentally, an image pickup range by the image pickup section 12 has a predetermined spread (a view angle) with respect to an observation point detected by the distance sensor 13. In order to specify an observation range, information concerning the view angle needs to be acquired. The information concerning the view angle of the image pickup section 12 may be acquired from the endoscope 2 or may be inputted by the input apparatus 30. In the endoscope 2, an ID generating section (in FIG. 2, simply abbreviated as ID) 15 configured by a ROM (read only memory) or the like configured to generate identification information (abbreviated as ID) peculiar to respective endoscopes 2 is provided. The ID generating section 15 outputs the ID to the position/direction acquisition circuit 25 in the image processing apparatus 5. Note that the ID generating section 15 may transmit the ID to the image processing apparatus 5 via the processor 4.

The position/direction acquisition circuit 25 has a function of an image-pickup-information acquiring section configured to acquire, from the ID, image pickup information in the case of image pickup by the image pickup section 12 such as a focal length of the objective optical system 10, the number of pixels of the image pickup device 11 configured to pick up an optical image by the objective optical system 10, a size of a pixel, and a view angle. The position/direction acquisition circuit 25 can output the acquired image pickup information to the control section 21. The control section 21 can use the image pickup information from the position/direction acquisition circuit 25 for calculation of an observation range.

A coordinate calculating section 21d in the control section 21 of the image processing apparatus 5 also functions as a coordinate-system converting section configured to convert a coordinate of the observation point calculated by the position/direction acquisition circuit 25 into a polar coordinate. In order to calculate a position of the orgin O and the coordinate axes X, Y, and Z of the polar coordinate, the coordinate calculating section 21d also has a function of an image analyzing section configured to perform an image analysis of an endoscopic image. The surgeon inserts the insertion section 2b into the bladder U and observes the internal urethral opening A, the left ureteral orifice B, the right ureteral orifice C, and the top T. The coordinate calculating section 21d reads out an endoscopic image obtained by the endoscope 2 from the memory 22, performs an image analysis, and detects that observation parts are the internal urethral opening A, the left ureteral orifice B, the right ureteral orifice C, and the top T, which are the four feature points of the bladder. The position/direction acquisition circuit 25 calculates positions of the internal urethral opening A, the left ureteral orifice B, the right ureteral orifice C, and the top T, gives a detection result of the positions to the position/direction-information storing section 22b of the memory 22, and causes the position/direction-information storing section 22b to store the detection result. The coordinate calculating section 21d calculates, on the basis of position information read out from the position/direction-information storing section 22b, a coordinate conversion formula for converting a coordinate system of the position/direction acquisition circuit into a coordinate system of the polar coordinate having the orgin O and the coordinate axes X, Y, and Z.

In the present embodiment, the orgin O and the coordinate axes X, Y, and Z of the polar coordinate do not change irrespective of expansion or reduction of the bladder U. Therefore, the coordinate conversion formula only has to be calculated only once for one patient. The coordinate conversion formula is stored in the memory 22 or another memory not shown in the figure.

When a coordinate is given from the position/direction acquisition circuit 25 during observation, the coordinate calculating section 21d converts the coordinate into a polar coordinate using the coordinate conversion formula. The coordinate calculating section 21d can calculate a polar coordinate of an observation point calculated on the basis of an output of the distance sensor 13 and calculate a polar coordinate of an observation range on the basis of information concerning a view angle of the image pickup section 12.

As model images, a two-dimensional (2D) image and a three-dimensional (3D image can be adopted. The model images are obtained by modeling an observation target organ. For example, the model image shown in FIG. 5 is adopted. A model-image generating section 21b reads out information concerning a model image from the 2D/3D-model-image storing section 22c of the memory 22 and generates display data for displaying the model image on the display screen of the monitor 6. The model-image generating section 21b outputs the model image to an image generating section 21c.

A polar coordinate of a photographing range is given to an indicator generating section 21a. The indicator generating section 21a generates data for display (hereinafter referred to as indicator data) for displaying an indicator indicating the photographing range on the model image. The indicator generating section 21a outputs the indicator data to the image generating section 21c. The image generating section 21c can display, on the monitor 6, the model image generated by the model-image generating section 21b and the endoscopic image read out from the memory 22, generate display data for displaying the indicator indicating the photographing range on the model image, and output the display data to the monitor 6 via the display I/F 23.

Note that the indicator generating section 21a may cause the memory 22 to store the indicator data. In this case, the image generating section 21c is capable of not only displaying an indicator indicating a region (the photographing range) currently being observed but also displaying, as indicators, ranges sequentially photographed in the past according to movement of the photographing range.

Figure 7:
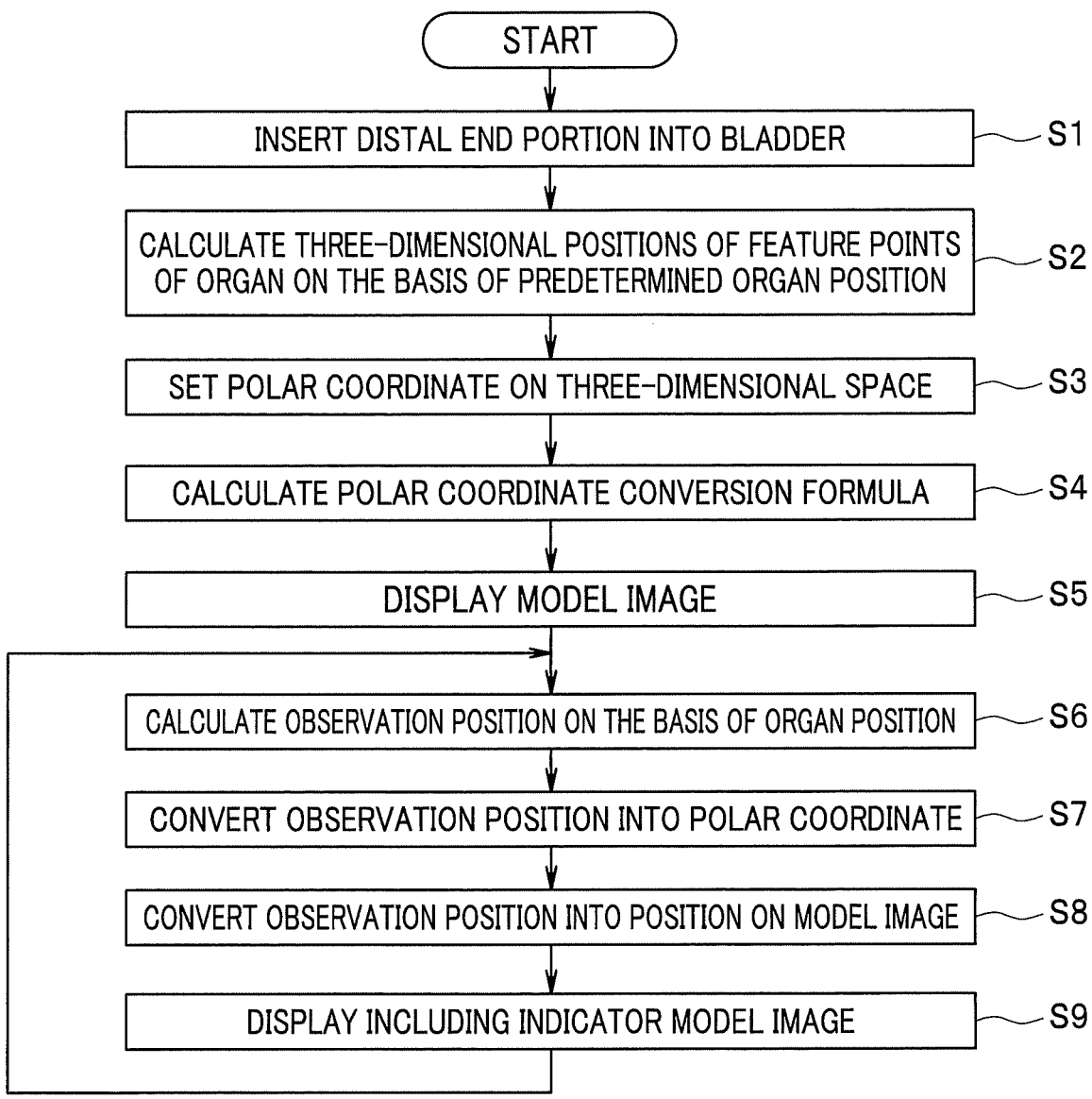
FIG. 7 is a flowchart showing an operation flow in the embodiment.
Figure 8:
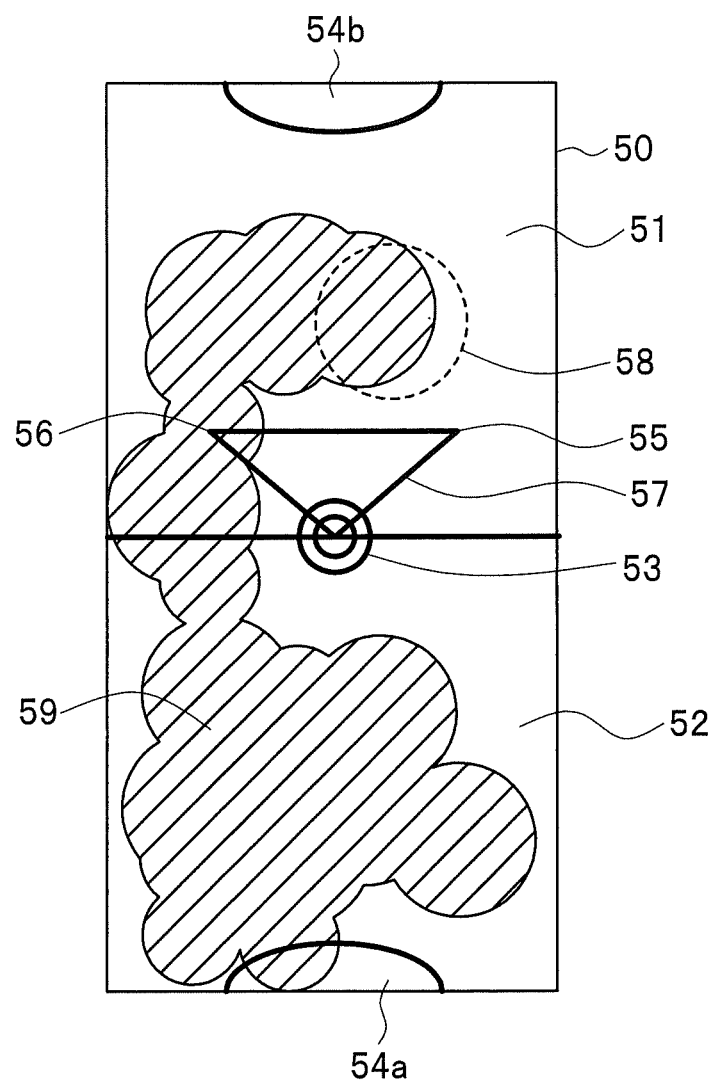
FIG. 8 is an explanatory diagram for explaining an indicator on a model image.

Operation in the embodiment configured as explained above is explained with reference to FIG. 7 and FIG. 8. FIG. 7 is a flowchart showing an operation flow in the present embodiment. FIG. 8 is an explanatory diagram for explaining an indicator on a model image.

When the medical apparatus 1 comes into an operation state, in a first step S1, the surgeon inserts the endoscope 2 into a urethra of the patient Pa. The position/direction acquisition circuit 25 detects, according to a detection result of the position-detecting-mechanism control section 27, a position and a direction of the distance sensor 13 at the distal end of the insertion section 2b on a three-dimensional coordinate system based on a predetermined measurement target reference position.

In order to set a polar coordinate, the surgeon picks up images of the internal urethral opening A, the left ureteral orifice B, the right ureteral orifice C, and the top T with the image pickup section 12 while changing a position and a direction of the insertion section 2b. Endoscopic images outputted from the image pickup section 12 are captured into the image processing apparatus 5 by the image capturing circuit 24 and sequentially stored in the endoscopic-image storing section 22a of the memory 22. Note that the image generating section 21c reads out the endoscopic images stored in the endoscopic-image storing section 22a and outputs the endoscopic images to the monitor 6 via the display I/F 23. In this way, the endoscopic image is displayed on the display screen of the monitor 6. The surgeon can perform insertion operation of the insertion section 2b while viewing the endoscopic image displayed on the display screen of the monitor 6.

The coordinate calculating section 21d of the control section 21 reads out the endoscopic images from the memory 22 and detects, with an image analysis, portions of the internal urethral opening A, the left ureteral orifice B, the right ureteral orifice C, and the top T, which are the feature points of the bladder U, from picked-up images. At detection points in time of the parts, the coordinate calculating section 21d acquires position information calculated by the position/direction acquisition circuit 25 on the basis of a position and a direction of the distance sensor 13 and distance information, that is, three-dimensional coordinates of the internal urethral opening A, the left ureteral orifice B, the right ureteral orifice C, and the top T in a coordinate system of the position/direction acquisition circuit (step S2).

In the next step S3, the coordinate calculating section 21d sets a polar coordinate on a three-dimensional space from the three-dimensional coordinates of the feature points of the bladder U. The origin O of the polar coordinate in this case is set in the organ deformation center of expansion and reduction of the bladder U. The respective coordinate axes are set to correspond to the model image of the bladder U as explained above. Subsequently, in step S4, the coordinate calculating section 21d calculates a polar coordinate conversion formula for converting a three-dimensional coordinate of the position/direction acquisition circuit into a polar coordinate.

In step S5, the model-image generating section 21b of the control section 21 reads out information stored in the 2D/3D-model-image storing section 22c, generates display data for displaying a model image, and outputs the display data to the monitor 6 via the image generating section 21c and the display I/F 23. In this way, the model image is displayed on the display screen of the monitor 6 together with the endoscopic image.

The position and the direction of the distance sensor 13 and the distance information calculated by the distance sensor 13 are sequentially given to the position/direction acquisition circuit 25. The position/direction acquisition circuit 25 acquires a three-dimensional coordinate of an observation point. Further, the position/direction acquisition circuit 25 acquires an ID of the endoscope 2 from the ID generating section 15 and acquires image pickup information in the case of image pickup by the image pickup section 12 such as a focal length of the objective optical system 10, the number of pixels of the image pickup device 11 configured to pick up an optical image by the objective optical system 10, a size of a pixel, and a view angle. The coordinate calculating section 21d calculates a three-dimensional coordinate of the observation range from these kinds of information and the three-dimensional coordinate of the observation point (step S6).

The coordinate calculating section 21d converts the three-dimensional coordinate of the observation range into a polar coordinate using the polar coordinate conversion formula (step S7). Further, the coordinate calculating section 21d converts the converted polar coordinate into information concerning a display position of the model image (step S8). The indicator generating section 21a generates display data for displaying an indicator indicating the observation range. In the present embodiment, display data of an indicator displayed on the model image is generated using information concerning θ and φ in the polar coordinate of the observation range obtained by the coordinate calculating section 21d.

The image generating section 21c displays, on the basis of the display data of the indicator generated by the indicator generating section 21a, an indicator indicating the observation range on the display screen of the monitor 6.

FIG. 8 shows a display example of a model image. A model image 50 includes a display region 51 of the posterior wall Wb in an upper part on the paper surface and a display region 52 of the anterior wall Wf in a lower part on the paper surface. Indication 53 corresponding to the internal urethral opening A is displayed on a boundary between the display regions 51 and 52. Triangular indication 57 connecting positions 55 and 56 respectively corresponding to the left ureteral orifice B and the right ureteral orifice C and a position of the indication 53 is displayed. Indication 54*b* corresponding to the top T is displayed at an upper end of the display region 51. Indication 54*a* corresponding to the top T is displayed at a lower end of the display region 52.

Indicator indication 58 indicating a present observation range with a broken line is displayed in the display region 51 of the posterior wall Wb. Indicator indication 59 in a shaded region indicates an observation range in the past.

The indicator indications 58 and 59 are obtained by measuring an observation range of an organ of the patient Pa by the endoscope 2 and performing coordinate conversion and can be displayed in accurate positions and ranges on the model image. Consequently, the surgeon can grasp accurate photographing ranges at present and in the past according to the indicator indications 58 and 59 on the model image 50 displayed on the monitor 6. The control section 21 can carry out the calculation of the photographing range on a real-time basis and can sequentially display a photographing range corresponding to the position and the direction of the endoscope insertion section 2*b* that change at every moment.

It is assumed that the bladder U expands or reduces because of perfusion or the like during observation. Even in this case, since the orgin O of the polar coordinate is set in the organ deformation center, unless the position and the direction of the insertion section 2*b* do not change, in the polar coordinate of the observation point, only r changes and θ and φ do not change. An indicator on the model image can be generated using only the information concerning θ and φ. Therefore, even when expansion or reduction of an organ occurs, a change of the model image, a change of the polar coordinate, and the like are unnecessary. It is possible to continuously display the indicator in an accurate position and an accurate range on the model image without suspending the observation.

Even when organs of different patients are observed, since the observation point is calculated in the polar coordinate and the indicator on the model image is generated using only the information concerning θ and φ, it is possible to display an indicator in an accurate position and an accurate range in the common model image.

As explained above, in the present embodiment, a position on the organ surface is specified by the polar coordinate system having the organ deformation center of expansion and reduction of the organ as the origin. Therefore, it is possible to display indication corresponding to the position on the organ surface in an accurate position and an accurate range in the common model image irrespective of expansion and reduction of the organ and irrespective of an individual difference of a size and a shape of the organ. Consequently, it is unnecessary to recreate a model image halfway in observation. It is possible to continuously perform observation and a surgical operation.

Second Embodiment

Figure 9A:
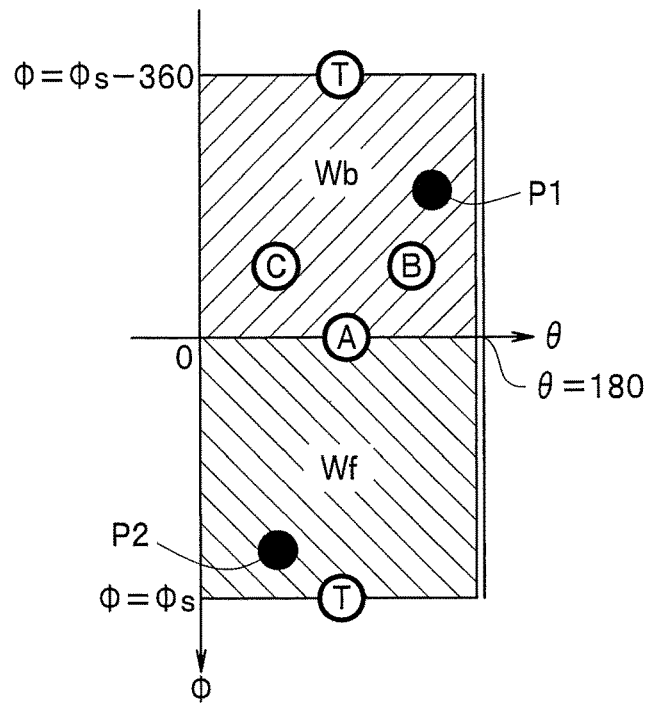
FIG. 9A is an explanatory diagram for explaining a model image adopted in a second embodiment of the present invention.
Figure 9B:
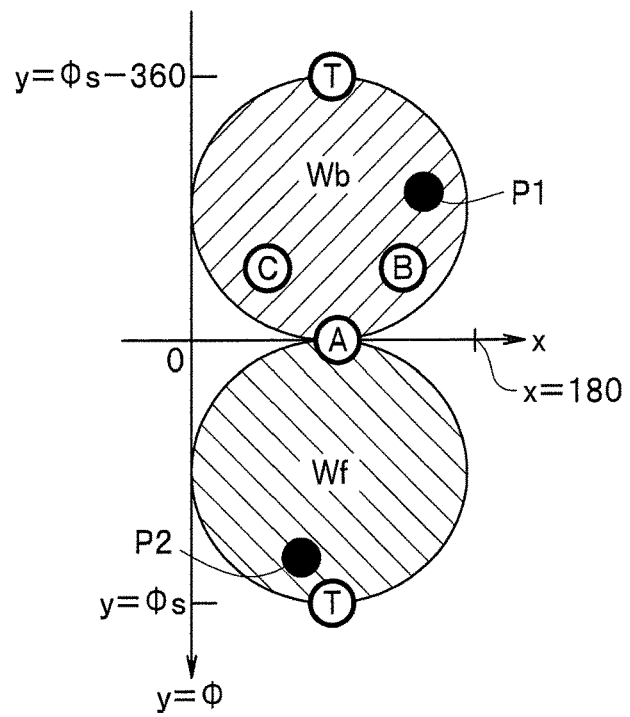
FIG. 9B is an explanatory diagram showing a model image adopted in the second embodiment of the present invention.

FIG. 9A is an explanatory diagram for explaining a model image adopted in a second embodiment of the present invention. FIG. 9B is an explanatory diagram showing a model image adopted in the second embodiment of the present invention. FIG. 9A shows a model image corresponding to FIG. 4, that is, an image same as the image shown in FIG. 5. A hardware configuration in the present embodiment is the same as the hardware configuration in the first embodiment.

In the first embodiment, the model image in which the anterior wall and the posterior wall have the square shape is adopted as the model image. The present embodiment is an example in which a model image in which an anterior wall and a posterior wall are represented by a circular shape is adopted.

The present embodiment is different from the first embodiment only in that the coordinate calculating section 21*d* additionally performs conversion processing from a model image having a square shape into a model image having a circular shape. That is, the coordinate calculating section 21*d* performs the conversion into the model image having the circular shape according to a conversion formula indicated by Equation (1) and Equation (2) described below.

$$y = \phi \quad (1)$$

In the following equation, x is a value obtained by correcting θ according to magnitude of y.

For example, when the square shape is converted into a perfect circle, in $\phi s - 360 < \phi < 0$ $$x = (\theta/90) + (90^2 - (y - (\phi s - 360)/2)^2)^{1/2}$$

in $0 < \phi < \phi s$ $$x = (\theta/90) \times (90^2 - (y - (\phi s)/2)^2)^{1/2} \quad (2)$$

FIG. 9B shows a model image after the conversion. The model image shown in FIG. 9B two-dimensionally displays the bladder U with x of the above Equation (2) plotted on a horizontal axis instead of θ and with y of the above Equation (1) plotted on a vertical axis instead of φ. In FIG. 9B, as in FIG. 9A, it is possible to show an observation point and the like in accurate positions on the model image.

Other configurations and action are the same as the configurations and the action in the first embodiment.

In the present embodiment, effects same as the effects in the first embodiment are obtained. As the model image, a circular image adopted in a schema of a bladder in general can be adopted.

Third Embodiment

Figure 10:
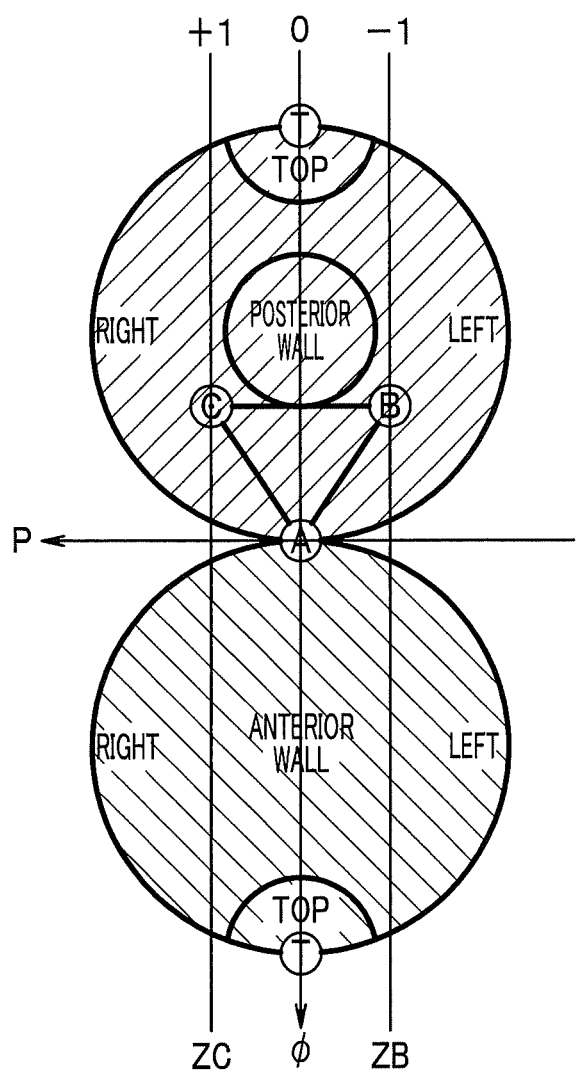
FIG. 10 is an explanatory diagram for explaining a third embodiment of the present invention.

FIG. 10 is an explanatory diagram for explaining a third embodiment of the present invention. A hardware configuration in the present embodiment is the same as the hardware configuration in the first embodiment.

In the first and second embodiments, the observation points and the like are accurately shown on the model image. That is, the predetermined observation point of the bladder U having the shape different from the shape of the model image is accurately shown on the model image by determining a position on the model image according to θ and φ of the polar coordinate. Therefore, in the first and second embodiments, an observation point on a line with a value of the Z axis of the polar coordinate fixed is shown as a point on a curved line on which θ changes to correspond to the distance r according to z=r×cos θ.

However, a doctor customarily determines a right lateral wall, an anterior wall or a posterior wall in a center, and a left lateral wall of the bladder U with two surfaces, which pass left and right urinary ducts and are parallel to the XY plane of the side shape U2 shown in FIG. 6, as a boundary and determines various examination results. On a schema of a paper medium, the doctor determines an outer side of a straight line in a longitudinal direction passing left and right ureteral orifices as a right or left lateral wall and performs diagnoses or the like. That is, when the observation point on the line with the Z axis of the polar coordinate fixed is located on a straight line with a coordinate value of a horizontal axis fixed of a model image, the doctor who has been using a schema of a bladder displayed on a paper medium can perform diagnoses and the like without having an unnatural feeling.

Therefore, in the present embodiment, in addition to the conversion processing from a model image having a square shape into a model image having a circular shape, the coordinate calculating section 21d performs correction such that an observation point on a line with a value of the Z axis fixed is located on a line with a coordinate value of the horizontal axis fixed of the model image. That is, when the observation point and the like are shown on the model image, the coordinate calculating section 21d uses $\phi$ of the polar coordinate as it is on the vertical axis of the model image and uses, on the horizontal axis, a value Z of a Z axis in an orthogonal coordinate having the X, Y, and Z axes of the polar coordinate as X, Y, and Z axes and plots P obtained by performing correction indicated by Equation (3) and Equation (4) described below.

When Z>0

$$P=Z/ZC \quad (3)$$

When Z≤0

$$P=Z/ZB \quad (4)$$

Note that P in the above Equation (3) and the above Equation (4) indicates a value on the horizontal axis of the model image, ZB indicates a value on the Z axis of the left ureteral orifice B, and ZC indicates a value on the Z axis of the right ureteral orifice C.

FIG. 10 shows a model image after the conversion. The model image shown in FIG. 10 two-dimensionally displays the bladder U with P of the above Equation (3) and the above Equation (4) plotted on a horizontal axis instead of θ and with $\phi$ plotted on a vertical axis. In the model image shown in FIG. 10, a line on which a value of a Z axis of an orthogonal coordinate is ZB is represented by a straight line with a value −1 on a P axis and a line on which the value of the Z axis of the orthogonal coordinate is ZC is represented by a straight line with a value +1 on the P axis. Consequently, a surgeon determines a region of P<−1 in the model image as a left lateral wall, determines a region of P>+1 as a right lateral wall, and, excluding the vicinity of the top T, determines a region of −1P<+1 and $\phi$≥0 is an anterior wall, and determines a region of −1≤P≤+1 and $\phi$≥0 as a posterior wall.

Other configurations and action are the same as the configurations and action in the second embodiment.

In the present embodiment, effects same as the effects in the second embodiment are obtained. Straight lines passing left and right urinary ducts can be displayed as straight lines on the model image as well. It is possible to facilitate determination of a right lateral wall, an anterior wall or a posterior wall in a center, and a left lateral wall of a bladder.

Note that, in the respective embodiments, the model image is explained using the two-dimensional image. However, a three-dimensional image may be adopted. As the two-dimensional model image, the images having the same shape are used on the anterior wall side and the posterior wall side. However, images having shapes and sizes different from each other may be adopted.

In the respective embodiments, the example is explained in which one polar coordinate is set in the entire organ assuming that the deformation center of the organ is one point. However, when there are a plurality of deformation centers of the organ, it is also possible that the organ is divided into a plurality of regions to correspond to the respective deformation centers, set a polar coordinate for each of the respective regions, calculate θ and $\phi$ of the polar coordinate of the observation point or the like for each of the respective regions, and show θ and $\phi$ on the model image.

In the respective embodiments, the observation range is explained as being displayed on the model image. However, a center position of the observation range, a designated part of the observation range, or the like may be displayed on the model image.

In the respective embodiments, the polar coordinate is explained as the spherical coordinate. However, the polar coordinate may be a columnar coordinate in the case of a tubular organ such as a large intestine. In that case, coordinate components are (r, θ, z). By displaying the organ on the model image with the angle components θ and z, it is possible to display the organ in a correct position irrespective of a bulge r in the radial direction of the large intestine.

In the respective embodiments, it is explained that, when the axes of the polar coordinate are determined, the z axis is determined first from C and B. However, the x axis may be determined first from A and 0.

The present invention is not limited to the embodiments per se. In an implementation stage, the constituent elements can be modified and embodied in a range not departing from the spirit of the present invention. Various inventions can be formed by appropriate combinations of the plurality of constituent elements disclosed in the embodiments. For example, several constituent elements may be deleted from all the constituent elements described in the embodiments.

In the techniques explained herein, most of the controls and the functions mainly explained in the flowcharts can be set by a program. The controls and the functions explained above can be realized by a computer reading and executing the program. The entire or a part of the program can be recorded or stored as a computer program product in a portable medium such as a flexible disk, a CD-ROM, or a nonvolatile memory or a storage medium such as a hard disk or a volatile memory and can be distributed or provided during product shipment or via a portable medium or a communication line. A user can easily realize the medical apparatus of the present embodiments by downloading the program via a communication network and installing the program in a computer or installing the program in the computer from a recording medium.

According to the present invention, there is an effect that it is possible to accurately indicate an observation range and the like using a common model image irrespective of deformation of an organ and even in an organ of a different person.

What is claimed is:
1. An endoscope apparatus comprising:
 a processor configured to:
  generate a two-dimensional model image having a circular shape obtained by modeling a shape of an inside of a subject;
  detect a three-dimensional position of a feature point of the inside of the subject;
  set a polar coordinate system on the basis of the three-dimensional position of the feature point;

calculate a polar coordinate of an arbitrary three-dimensional position of the inside of the subject in the set polar coordinate system;

set two angle components of the calculated polar coordinate as two components obtained when a position on a two-dimensional model image having a square shape obtained by modeling the shape of the inside of the subject is expressed by an orthogonal coordinate, and convert the position on the two-dimensional model image having the square shape to a position on the two-dimensional model image having the circular shape by:

setting one of the two angle components of the polar coordinate as one of the two components of the orthogonal coordinate; and calculating the other of the two components of the orthogonal coordinate by correcting the other of the two angle components on the basis of a difference in shape between the square shape and the circular shape according to a size of the one of the two components of the orthogonal coordinate; and control a display to display the arbitrary three-dimensional position of the inside of the subject on the two-dimensional model image having the circular shape on the basis of the calculated two components of the orthogonal coordinate.

2. The endoscope apparatus according to claim 1, further comprising a position/direction acquiring circuit configured to calculate the arbitrary three-dimensional position of the inside of the subject including the feature point.

3. The endoscope apparatus according to claim 1, further comprising an insertion section configured to be inserted into the inside of the subject, wherein the insertion section comprises an image sensor configured to acquire an image of the inside of the subject, and wherein the processor is configured to detect the feature point according to an image analysis of the image of the inside of the subject acquired by the image sensor.

4. The endoscope apparatus according to claim 3, further comprising a position/direction acquiring circuit configured to calculate arbitrary three-dimensional positions of the inside of the subject including the feature point on the basis of a reference position fixed with respect to a predetermined position of the inside of the subject.

5. The endoscope apparatus according to claim 4, wherein the position/direction acquiring circuit is configured to:

calculate distances from the image sensor to the arbitrary three-dimensional positions of the inside of the subject; and calculate the arbitrary three-dimensional positions of the inside of the subject on the basis of the calculated distances and a three-dimensional position and a direction of the image sensor.

6. The endoscope apparatus according to claim 3, wherein the processor is configured to control the display to display an indicator indicating an observation range of the image sensor on the two-dimensional model image having the circular shape.

7. An endoscope apparatus comprising:

a processor configured to:

generate a two-dimensional model image having a circular shape obtained by modeling a shape of an inside of a subject;

detect a three-dimensional position of a feature point of the inside of the subject;

set a polar coordinate on the basis of a position of the feature point;

calculate the polar coordinate of an arbitrary three-dimensional position of the inside of the subject;

set two angle components of the calculated polar coordinate as two components obtained when a position on a two-dimensional model image having a square shape obtained by modeling the shape of the inside of the subject is expressed by an orthogonal coordinate;

convert the position on the two-dimensional model image having the square shape to a position on the two-dimensional model image having the circular shape and to make linear a position of the two-dimensional model image having the circular shape corresponding to a same value as one of the two angle components of the polar coordinate by;

setting the one of the two angle components of the polar coordinate as one of the two components of the orthogonal coordinate; and calculating the other of the two components of the orthogonal coordinate by a calculation on the one of the two components of the orthogonal coordinate obtained by converting the polar coordinate; and control a display to show the arbitrary three-dimensional position of the inside of the subject on the two-dimensional model image having the circular shape on the basis of the calculated two components of the orthogonal coordinate.

8. A medical-image generating method comprising:

calculating an arbitrary three-dimensional position of an inside of a subject including a feature point of the inside of the subject;

setting a polar coordinate on the basis of a three-dimensional position of the feature point of the inside of the subject;

calculating the polar coordinate of the arbitrary three-dimensional position of the inside of the subject;

setting two angle components of the calculated polar coordinate as two components obtained when a position on a two-dimensional model image having a square shape obtained by modeling the shape of the inside of the subject is expressed by an orthogonal coordinate;

converting the position on the two-dimensional model image having the square shape to a position on the two-dimensional model image having a circular shape by:

setting one of the two angle components of the polar coordinate as one of the two components of the orthogonal coordinate; and calculating the other of the two components of the orthogonal coordinate by correcting the other of the two angle components on the basis of a difference in shape between the square shape and the circular shape according to a size of the one of the two components of the orthogonal coordinate; and generating the two-dimensional model image having the circular shape obtained by modeling a shape of the inside of the subject; and controlling a display to show the arbitrary three-dimensional position of the inside of the subject on the two-dimensional model image having the circular shape on the basis of the calculated two components of the orthogonal coordinate.

9. A non-transitory computer-readable recording medium on which a medical-image generating program is recorded, the medical-image generating program being for causing a computer to at least execute:

calculating an arbitrary three-dimensional position of an inside of a subject including a feature point of the inside of the subject;

setting a polar coordinate on the basis of a three-dimensional position of the feature point of the inside of the subject and calculating the polar coordinate of the arbitrary three-dimensional position of the inside of the subject, setting two angle components of the calculated polar coordinate as two components obtained when a position on a two-dimensional model image having a square shape obtained by modeling the shape of the inside of the subject is expressed by an orthogonal coordinate;

converting the position on the two-dimensional model image having the square shape to a position on a two-dimensional model image having the circular shape by:

setting one of the two angle components of the polar coordinate as one of the two components of the orthogonal coordinate; and calculating the other of the two components of the orthogonal coordinate by correcting the other of the two angle components on the basis of a difference in shape between the square shape and the circular shape according to a size of the one of the two components of the orthogonal coordinate; and generating the two-dimensional model image having the circular shape obtained by modeling a shape of the inside of the subject; and controlling a display to show the arbitrary three-dimensional position of the inside of the subject on the two-dimensional model image having the circular shape on the basis of the calculated two components of the orthogonal coordinate.

\* \* \* \* \*